United States Patent [19]
Fischer et al.

[11] Patent Number: 5,912,373
[45] Date of Patent: *Jun. 15, 1999

[54] PROCESS FOR CONVERTING THE ACHIRAL MESO FORM OF AN ANSA-METALLOCENE COMPLEX INTO THE CHIRAL RACEMIC FORM

[75] Inventors: David Fischer, Gönnheim; Franz Langhauser, Bad Dürkheim; Jürgen Kerth, Carlsberg; Günther Schweier, Friedelsheim, all of Germany; Hans-Herbert Brintzinger, Taegerswilen, Switzerland; Katrin Schmidt, Konstanz, Germany

[73] Assignee: BASF Aktiengesellschaft, Ludwigshafen, Germany

[*] Notice: This patent is subject to a terminal disclaimer.

[21] Appl. No.: 08/981,100
[22] PCT Filed: Jul. 1, 1996
[86] PCT No.: PCT/EP96/02868
  § 371 Date: Dec. 17, 1997
  § 102(e) Date: Dec. 17, 1997
[87] PCT Pub. No.: WO97/03080
  PCT Pub. Date: Jan. 30, 1997

[30] Foreign Application Priority Data

Jul. 11, 1995 [DE] Germany ............... 195 25 178

[51] Int. Cl.⁶ ............... C07F 17/00; C07F 11/00; C07F 7/28
[52] U.S. Cl. ............... 556/7; 556/11; 556/12; 556/13; 556/27; 556/28; 556/43; 556/53; 556/54; 502/103; 502/117; 502/152; 502/162; 526/160; 526/943
[58] Field of Search ............... 556/7, 11, 12, 556/13, 21, 27, 28, 43, 53, 54; 502/103, 117, 152, 162; 526/160, 943

[56] References Cited

U.S. PATENT DOCUMENTS 5,302,733  4/1994  Diefenbach et al. ............... 556/11

FOREIGN PATENT DOCUMENTS

| 444474 | 9/1991 | European Pat. Off. . |
| 485823 | 5/1992 | European Pat. Off. . |
| 519237 | 12/1992 | European Pat. Off. . |
| 576970 | 1/1994 | European Pat. Off. . |
| 5287017 | 4/1992 | Japan . |

OTHER PUBLICATIONS

J. of Organomet. Chem., 369, 1989, pp. 359–370.
Organometallics, 11, pp. 3600–3607, 1992.
J. of Organomet. Chem., 342, pp. 21–29, 1988.
J. of Organomet. Chem., 232, 1982, pp. 233–247.
Makromol. Chem., vol. 8, 1987, pp. 305–310.
J. of Am. Chem. Soc., vol. 114, 1992, pp. 9300–9304.
Organometallics, 14, 1995, pp. 5–7.
Organometallics, 13(10), 1994, pp. 3892–3896.
J. Am. Chem. Soc., 112, 1990, pp. 4911–4914.

Primary Examiner—Porfirio Nazario-Gonzalez
Attorney, Agent, or Firm—Keil & Weinkauf

[57] ABSTRACT

The conversion of the achiral meso form of an ansa-metallocene complex into the chiral rac form is carried out photochemically in the presence of a chiral auxiliary reagent.

9 Claims, No Drawings

PROCESS FOR CONVERTING THE ACHIRAL MESO FORM OF AN ANSA-METALLOCENE COMPLEX INTO THE CHIRAL RACEMIC FORM

This application was filed as a request for U.S. examination under 35 U.S.C. § 371 of International application No. PCT/EP96/02868 filed Jul. 01, 1996.

The present invention relates to a process for converting the achiral meso form of an ansa-metallocene complex into the chiral rac form.

Chiral ansa-metallocene complexes of metals of transition group IV of the Periodic Table of the Elements have in recent years attracted great interest as effective catalysts for stereospecific olefin polymerization, as described in EP-A 444 474, EP-A 519 237 and EP-A 576 970. They make it possible to prepare chemically uniform polyolefins of high isotacticity. However, in the synthesis of such metallocene complexes, considerable amounts of the achiral meso compound are usually obtained, as a result of which the yield of chiral metallocene complexes is significantly reduced. Since these meso forms generally catalyze nonstereospecific 1-olefin polymerization, they have to be separated off before the racemate of the metallocene complex can be used as polymerization catalyst (EP-A 485 823).

There have been many attempts in the past to improve the rac/meso diastereomer ratio in the ansa-metallocene synthesis, or at least to avoid the need to remove the meso compound. Introducing an alkyl substituent in the α position of the cyclopentadienyl ring enabled the rac/meso ratio to be increased to significantly above 1.0, as described in Brintzinger et al, Journal of Organometallic Chemistry, 369 (1989), pp. 359–370. A disadvantage here is that the method significantly restricts the freedom with which the ligands may be structured. In addition, despite the improved yield of racemic diastereomers, appreciable amounts (33–15%) of the meso complex are still formed.

Better yields of the racemic diastereomers were able to be achieved by reacting $Zr(NMe_2)_4$ with 1,2-bisindenylethane, as described in Jordan et al., Organometallics, 14 (1995), pp. 5–7. Disadvantages are the great sensitivity and the high price of the tetrakis(dimethylamido)zirconium used. Furthermore, diastereoselective syntheses of chiral ansa-metallocenes are known only for very few, specific ligand systems which are described, for example, in Brintzinger et al., Organometallics 11 (1992), pp. 3600–3607; S. Buchwald et al., Organometallics 13 (1994), (10), pp. 3892–3840 and in U.S. Pat. No. 5,302,733.

In some cases, the yield of racemate could be increased by photochemical conversion of the undesired meso form into the rac form, as described in S. Collins et al., Journal of Organometallic Chemistry 342 (1988), pp. 21–29. However, here too, the rac form is obtained only in thermodynamic equilibrium with the meso diastereomer. Quantitative isomerization to the rac form is not possible by this route.

It is an object of the present invention to provide a process for quantitatively converting the undesired meso form of an ansa-metallocene complex into the desired rac form; this conversion should be technically simple in terms of the process and be inexpensive.

We have found that this object is achieved by a process for converting the achiral meso form of an ansa-metallocene complex into the chiral rac form, wherein the conversion is carried out photochemically in the presence of a chiral auxiliary reagent.

The terms "meso form" and "rac form" in the context of ansa-metallocene complexes are known and described, for example, in Brintzinger et al., Journal of Organometallic Chemistry, 369 (1989), pp. 359–370.

ansa-Metallocene complexes which are particularly suitable for use in the process of the present invention are those of the formula I

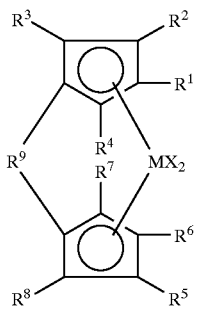

where the substituents and indices have the following meanings:

M is titanium, zirconium, hafnium, vanadium, niobium or tantalum,

X is fluorine, chlorine, bromine, iodine, hydrogen, $C_1$–$C_{10}$-alkyl, $C_6$–$C_{15}$-aryl or —$OR^{10}$,
   where $R^{10}$ is $C_1$–$C_{10}$-alkyl, $C_6$–$C_{15}$-aryl, alkylaryl, arylalkyl, fluoroalkyl or fluoroaryl each having from 1 to 10 carbon atoms in the alkyl radical and from 6 to 20 carbon atoms in the aryl radical, $R^1$ to $R^8$ are hydrogen, $C_1$–$C_{10}$-alkyl, 5- to 7-membered cycloalkyl which may in turn bear a $C_1$–$C_{10}$-alkyl group as substituent, $C_6$–$C_{15}$-aryl or arylalkyl, where two adjacent radicals may together form a cyclic group having from 4 to 15 carbon atoms, or $Si(R^{11})_3$ where $R^{11}$ is $C_1$–$C_{10}$-alkyl, $C_6$–$C_{15}$-aryl or $C_3$–$C_{10}$-cycloalkyl, $R^9$

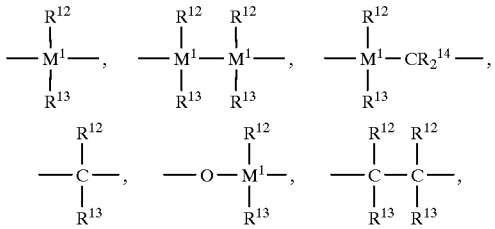

=$BR^{12}$, =$AlR^{12}$, —Ge—, —Sn—, —O—, —S—, =SO, =$SO_2$, =$NR^{12}$, =CO, =$PR^{12}$ or =P(O)$R^{12}$, where $R^{12}$, $R^{13}$ and $R^{14}$ are identical or different and are hydrogen, halogen, $C_1$–$C_{10}$-alkyl, $C_1$–$C_{10}$-fluoroalkyl, $C_6$–$C_{10}$-fluoroaryl, $C_6$–$C_{10}$-aryl, $C_1$–$C_{10}$-alkoxy, $C_2$–$C_{10}$-alkenyl, $C_7$–$C_{40}$-arylalkyl, $C_8$–$C_{40}$-arylalkenyl or $C_7$–$C_{40}$-alkylaryl, or $R^{12}$ and $R^{13}$ or $R^{12}$ and $R^{14}$ in each case together with the atoms connecting them form a ring, and $M^1$ is silicon, germanium or tin.

Particularly suitable ansa-metallocene complexes of the formula I, are those in which M is titanium, zirconium or hafnium, X is chlorine or $C_1$–$C_6$-alkyl, $R^1$ to $R^8$ are hydrogen, $C_1$–$C_6$-alkyl, $C_1$–$C_{12}$-aryl or two adjacent radicals together form a cyclic group having from 4 to 15 carbon atoms, in particular from 8 to 12 carbon atoms,
and $M^1$ is silicon.

Preference is given to ansa-metallocene complexes of the formula I which are substituted in the 2 position of the cyclopentadienyl rings, ie. $R^4$ and $R^7$ in the formula I are different from hydrogen and are, in particular, methyl, ethyl, n-propyl, iso-propyl, n-butyl, tert-butyl or phenyl.

Furthermore, preference is given to those ansa-metallocene complexes which are silyl-bridged, ie. $M^1$ is silicon.

Examples of particularly useful ansa-metallocene complexes are, inter alia:

dimethylsilanediylbis(2-methyl-4-methyl-1-cyclopentadienyl)zirconium dichloride
dimethylsilanediylbis(2-methyl-4-ethyl-1-cyclopentadienyl)zirconium dichloride
dimethylsilanediylbis(2-methyl-4-propyl-1-cyclopentadienyl)zirconium dichloride
dimethylsilanediylbis(2-methyl-4-butyl-1-cyclopentadienyl)zirconium dichloride
dimethylsilanediylbis(2-methyl-4-i-propyl-1-cyclopentadienyl)zirconium dichloride
dimethylsilanediylbis(2-methyl-4-i-butyl-1-cyclopentadienyl)zirconium dichloride
dimethylsilanediylbis(2-methyl-4-t-butyl-1-cyclopentadienyl)zirconium dichloride
dimethylsilanediylbis(2-methyl-4-trimethylsilyl-1-cyclopentadienyl)zirconium dichloride
dimethylsilanediylbis(2-methyl-4-phenyl-1-cyclopentadienyl)zirconium dichloride
dimethylsilanediylbis(2-ethyl-4-methyl-1-cyclopentadienyl)zirconium dichloride
dimethylsilanediylbis(2-ethyl-4-ethyl-1-cyclopentadienyl)zirconium dichloride
dimethylsilanediylbis(2-ethyl-4-propyl-1-cyclopentadienyl)zirconium dichloride
dimethylsilanediylbis(2-ethyl-4-butyl-1-cyclopentadienyl)zirconium dichloride
dimethylsilanediylbis(2-ethyl-4-i-propyl-1-cyclopentadienyl)zirconium dichloride
dimethylsilanediylbis(2-ethyl-4-i-butyl-1-cyclopentadienyl)zirconium dichloride
Dimethylsilanediylbis(2-ethyl-4-t-butyl-1-cyclopentadienyl)zirconium dichloride
dimethylsilanediylbis(2-ethyl-4-trimethylsilyl-1-cyclopentadienyl)zirconium dichloride
dimethylsilanediylbis(2-ethyl-4-phenyl-1-cyclopentadienyl)zirconium dichloride
dimethylsilanediylbis(2-propyl-4-methyl-1-cyclopentadienyl)zirconium dichloride
dimethylsilanediylbis(2-propyl-4-ethyl-1-cyclopentadienyl)zirconium dichloride
dimethylsilanediylbis(2-propyl-4-propyl-1-cyclopentadienyl)zirconium dichloride
dimethylsilanediylbis(2-propyl-4-butyl-1-cyclopentadienyl)zirconium dichloride
dimethylsilanediylbis(2-propyl-4-i-propyl-1-cyclopentadienyl)zirconium dichloride
dimethylsilanediylbis(2-propyl-4-i-butyl-1-cyclopentadienyl)zirconium dichloride
dimethylsilanediylbis(2-propyl-4-t-butyl-1-cyclopentadienyl)zirconium dichloride
dimethylsilanediylbis(2-propyl-4-trimethylsilyl-1-cyclopentadienyl)zirconium dichloride
dimethylsilanediylbis(2-propyl-4-phenyl-1-cyclopentadienyl)zirconium dichloride
dimethylsilanediylbis(2-butyl-4-methyl-1-cyclopentadienyl)zirconium dichloride
dimethylsilanediylbis(2-butyl-4-ethyl-1-cyclopentadienyl)zirconium dichloride
dimethylsilanediylbis(2-butyl-4-propyl-1-cyclopentadienyl)zirconium dichloride
dimethylsilanediylbis(2-butyl-4-butyl-1-cyclopentadienyl)zirconium dichloride
dimethylsilanediylbis(2-butyl-4-i-propyl-1-cyclopentadienyl)zirconium dichloride
dimethylsilanediylbis(2-butyl-4-i-butyl-1-cyclopentadienyl)zirconium dichloride
dimethylsilanediylbis(2-butyl-4-t-butyl-1-cyclopentadienyl)zirconium dichloride
dimethylsilanediylbis(2-butyl-4-trimethylsilyl-1-cyclopentadienyl)zirconium dichloride
dimethylsilanediylbis(2-butyl-4-phenyl-1-cyclopentadienyl)zirconium dichloride
dimethylsilanediylbis(2-i-propyl-4-methyl-1-cyclopentadienyl)zirconium dichloride
dimethylsilanediylbis(2-i-propyl-4-ethyl-1-cyclopentadienyl)zirconium dichloride
dimethylsilanediylbis(2-i-propyl-4-propyl-1-cyclopentadienyl)zirconium dichloride
dimethylsilanediylbis(2-i-propyl-4-butyl-1-cyclopentadienyl)zirconium dichloride
Dimethylsilanediylbis(2-i-propyl-4-i-propyl-1-cyclopentadienyl)zirconium dichloride
dimethylsilanediylbis(2-i-propyl-4-i-butyl-1-cyclopentadienyl)zirconium dichloride
dimethylsilanediylbis(2-i-propyl-4-t-butyl-1-cyclopentadienyl)zirconium dichloride
dimethylsilanediylbis(2-i-propyl-4-trimethylsilyl-1-cyclopentadienyl)zirconium dichloride
dimethylsilanediylbis(2-i-propyl-4-phenyl-1-cyclopentadienyl)zirconium dichloride
dimethylsilanediylbis(2-t-butyl-4-methyl-1-cyclopentadienyl)zirconium dichloride
dimethylsilanediylbis(2-t-butyl-4-ethyl-1-cyclopentadienyl)zirconium dichloride
dimethylsilanediylbis(2-t-butyl-4-propyl-1-cyclopentadienyl)zirconium dichloride
dimethylsilanediylbis(2-t-butyl-4-butyl-1-cyclopentadienyl)zirconium dichloride
dimethylsilanediylbis(2-t-butyl-4-i-propyl-1-cyclopentadienyl)zirconium dichloride
dimethylsilanediylbis(2-t-butyl-4-i-butyl-1-cyclopentadienyl)zirconium dichloride
dimethylsilanediylbis(2-t-butyl-4-t-butyl-1-cyclopentadienyl)zirconium dichloride
dimethylsilanediylbis(2-t-butyl-4-trimethylsilyl-1-cyclopentadienyl)zirconium dichloride
dimethylsilanediylbis(2-t-butyl-4-phenyl-1-cyclopentadienyl)zirconium dichloride
dimethylsilanediylbis(2-trimethylsilyl-4-methyl-1-cyclopentadienyl)zirconium dichloride
dimethylsilanediylbis(2-trimethylsilyl-4-ethyl-1-cyclopentadienyl)zirconium dichloride
dimethylsilanediylbis(2-trimethylsilyl-4-propyl-1-cyclopentadienyl)zirconium dichloride
dimethylsilanediylbis(2-trimethylsilyl-4-butyl-1-cyclopentadienyl)zirconium dichloride
dimethylsilanediylbis(2-trimethylsilyl-4-i-propyl-1-cyclopentadienyl)zirconium dichloride
dimethylsilanediylbis(2-trimethylsilyl-4-i-butyl-1-cyclopentadienyl)zirconium dichloride
dimethylsilanediylbis(2-trimethylsilyl-4-t-butyl-1-cyclopentadienyl)zirconium dichloride dimethylsilanediylbis(2-trimethylsilyl-4-trimethylsilyl-1-cyclopentadienyl)zirconium dichloride
dimethylsilanediylbis(2-trimethylsilyl-4-phenyl-1-cyclopentadienyl)zirconium dichloride
dimethylsilanediylbis(2-phenyl-4-methyl-1-cyclopentadienyl)zirconium dichloride
dimethylsilanediylbis(2-phenyl-4-ethyl-1-cyclopentadienyl)zirconium dichloride
dimethylsilanediylbis(2-phenyl-4-propyl-1-cyclopentadienyl)zirconium dichloride
dimethylsilanediylbis(2-phenyl-4-butyl-1-cyclopentadienyl)zirconium dichloride
dimethylsilanediylbis(2-phenyl-4-i-propyl-1-cyclopentadienyl)zirconium dichloride
dimethylsilanediylbis(2-phenyl-4-i-butyl-1-cyclopentadienyl)zirconium dichloride
dimethylsilanediylbis(2-phenyl-4-t-butyl-1-cyclopentadienyl)zirconium dichloride
dimethylsilanediylbis(2-phenyl-4-trimethylsilyl-1-cyclopentadienyl)zirconium dichloride
dimethylsilanediylbis(2-phenyl-4-phenyl-1-cyclopentadienyl)zirconium dichloride
dimethylsilanediylbis(2-methyl-1-indenyl)zirconium dichloride
dimethylsilanediylbis(2-ethyl-1-indenyl)zirconium dichloride
dimethylsilanediylbis(2-propyl-1-indenyl)zirconium dichloride
dimethylsilanediylbis(2-butyl-1-indenyl)zirconium dichloride
dimethylsilanediylbis(2-i-propyl-1-indenyl)zirconium dichloride
dimethylsilanediylbis(2-t-butyl-1-indenyl)zirconium dichloride
dimethylsilanediylbis(2-trimethylsilyl-1-indenyl)zirconium dichloride
dimethylsilanediylbis(2-phenyl-1-indenyl)zirconium dichloride
dimethylsilanediylbis(2-methyl-4,5,6,7-tetrahydro-1-indenyl)zirconium dichloride
dimethylsilanediylbis(2-ethyl-4,5,6,7-tetrahydro-1-indenyl)zirconium dichloride
dimethylsilanediylbis(2-propyl-4,5,6,7-tetrahydro-1-indenyl)zirconium dichloride
dimethylsilanediylbis(2-butyl-4,5,6,7-tetrahydro-1-indenyl)zirconium dichloride
dimethylsilanediylbis(2-i-propyl-4,5,6,7-tetrahydro-1-indenyl)zirconium dichloride
dimethylsilanediylbis(2-t-butyl-4,5,6,7-tetrahydro-1-indenyl)zirconium dichloride
dimethylsilanediylbis(2-trimethylsilyl-4,5,6,7-tetrahydro-1-indenyl)zirconium dichloride
dimethylsilanediylbis(2-phenyl-4,5,6,7-tetrahydro-1-indenyl)zirconium dichloride
dimethylsilanediylbis(2-methyl-4,7-dimethyl-1-indenyl)zirconium dichloride
dimethylsilanediylbis(2-ethyl-4,7-dimethyl-1-indenyl)zirconium dichloride
dimethylsilanediylbis(2-propyl-4,7-dimethyl-1-indenyl)zirconium dichloride
dimethylsilanediylbis(2-butyl-4,7-dimethyl-1-indenyl)zirconium dichloride
dimethylsilanediylbis(2-i-propyl-4,7-dimethyl-1-indenyl)zirconium dichloride
dimethylsilanediylbis(2-t-butyl-4,7-dimethyl-1-indenyl)zirconium dichloride
dimethylsilanediylbis(2-trimethylsilyl-4,7-dimethyl-1-indenyl)zirconium dichloride
dimethylsilanediylbis(2-phenyl-4,7-dimethyl-1-indenyl)zirconium dichloride
dimethylsilanediylbis(2-methyl-4,6-di-i-propyl-1-indenyl)zirconium dichloride
dimethylsilanediylbis(2-ethyl-4,6-di-i-propyl-1-indenyl)zirconium dichloride
dimethylsilanediylbis(2-propyl-4,6-di-i-propyl-1-indenyl)zirconium dichloride
dimethylsilanediylbis(2-butyl-4,6-di-i-propyl-1-indenyl)zirconium dichloride
dimethylsilanediylbis(2-i-propyl-4,6-di-i-propyl-1-indenyl)zirconium dichloride
dimethylsilanediylbis(2-t-butyl-4,6-di-i-propyl-1-indenyl)zirconium dichloride
dimethylsilanediylbis(2-trimethylsilyl-4,6-di-i-propyl-1-indenyl)zirconium dichloride
dimethylsilanediylbis(2-phenyl-4,6-di-i-propyl-1-indenyl)zirconium dichloride
dimethylsilanediylbis(2-methyl-1-benzindenyl)zirconium dichloride
dimethylsilanediylbis(2-ethyl-1-benzindenyl)zirconium dichloride
dimethylsilanediylbis(2-propyl-1-benzindenyl)zirconium dichloride
dimethylsilanediylbis(2-butyl-1-benzindenyl)zirconium dichloride
dimethylsilanediylbis(2-i-propyl-1-benzindenyl)zirconium dichloride
dimethylsilanediylbis(2-t-butyl-1-benzindenyl)zirconium dichloride
dimethylsilanediylbis(2-trimethylsilyl-1-benzindenyl)zirconium dichloride
dimethylsilanediylbis(2-phenyl-1-benzindenyl)zirconium dichloride
dimethylsilanediylbis(2-methyl-4-phenyl-1-indenyl)zirconium dichloride
dimethylsilanediylbis(2-ethyl-4-phenyl-1-indenyl)zirconium dichloride
dimethylsilanediylbis(2-propyl-4-phenyl-1-indenyl)zirconium dichloride
dimethylsilanediylbis(2-butyl-4-phenyl-1-indenyl)zirconium dichloride
dimethylsilanediylbis(2-i-propyl-4-phenyl-1-indenyl)zirconium dichloride
dimethylsilanediylbis(2-t-butyl-4-phenyl-1-indenyl)zirconium dichloride
dimethylsilanediylbis(2-trimethylsilyl-4-phenyl-1-indenyl)zirconium dichloride
dimethylsilanediylbis(2-phenyl-4-phenyl-1-indenyl)zirconium dichloride
dimethylsilanediylbis(2-methyl-4-naphthyl-1-indenyl)zirconium dichloride
dimethylsilanediylbis(2-ethyl-4-naphthyl-1-indenyl)zirconium dichloride
dimethylsilanediylbis(2-propyl-4-naphthyl-1-indenyl)zirconium dichloride
dimethylsilanediylbis(2-butyl-4-naphthyl-1-indenyl)zirconium dichloride
dimethylsilanediylbis(2-i-propyl-4-naphthyl-1-indenyl)zirconium dichloride
dimethylsilanediylbis(2-t-butyl-4-naphthyl-1-indenyl)zirconium dichloride
dimethylsilanediylbis(2-trimethylsilyl-4-naphthyl-1-indenyl)zirconium dichloride
dimethylsilanediylbis(2-phenyl-4-naphthyl-1-indenyl)zirconium dichloride
dimethylsilanediylbis(2-methyl-4-methyl-1-cyclopentadienyl)titanium dichloride dimethylsilanediylbis(2-methyl-4-ethyl-1-cyclopentadienyl)titanium dichloride
dimethylsilanediylbis(2-methyl-4-propyl-1-cyclopentadienyl)titanium dichloride
dimethylsilanediylbis(2-methyl-4-butyl-1-cyclopentadienyl)titanium dichloride
dimethylsilanediylbis(2-methyl-4-i-propyl-1-cyclopentadienyl)titanium dichloride
dimethylsilanediylbis(2-methyl-4-i-butyl-1-cyclopentadienyl)titanium dichloride
dimethylsilanediylbis(2-methyl-4-t-butyl-1-cyclopentadienyl)titanium dichloride
dimethylsilanediylbis(2-methyl-4-trimethylsilyl-1-cyclopentadienyl)titanium dichloride
dimethylsilanediylbis(2-methyl-4-phenyl-1-cyclopentadienyl)titanium dichloride
dimethylsilanediylbis(2-ethyl-4-methyl-1-cyclopentadienyl)titanium dichloride
dimethylsilanediylbis(2-ethyl-4-ethyl-1-cyclopentadienyl)titanium dichloride
dimethylsilanediylbis(2-ethyl-4-propyl-1-cyclopentadienyl)titanium dichloride
dimethylsilanediylbis(2-ethyl-4-butyl-1-cyclopentadienyl)titanium dichloride
dimethylsilanediylbis(2-ethyl-4-i-propyl-1-cyclopentadienyl)titanium dichloride
dimethylsilanediylbis(2-ethyl-4-i-butyl-1-cyclopentadienyl)titanium dichloride
dimethylsilanediylbis(2-ethyl-4-t-butyl-1-cyclopentadienyl)titanium dichloride
dimethylsilanediylbis(2-ethyl-4-trimethylsilyl-1-cyclopentadienyl)titanium dichloride
dimethylsilanediylbis(2-ethyl-4-phenyl-1-cyclopentadienyl)titanium dichloride
dimethylsilanediylbis(2-propyl-4-methyl-1-cyclopentadienyl)titanium dichloride
dimethylsilanediylbis(2-propyl-4-ethyl-1-cyclopentadienyl)titanium dichloride
dimethylsilanediylbis(2-propyl-4-propyl-1-cyclopentadienyl)titanium dichloride
dimethylsilanediylbis(2-propyl-4-butyl-1-cyclopentadienyl)titanium dichloride
dimethylsilanediylbis(2-propyl-4-i-propyl-1-cyclopentadienyl)titanium dichloride
dimethylsilanediylbis(2-propyl-4-i-butyl-1-cyclopentadienyl)titanium dichloride
dimethylsilanediylbis(2-propyl-4-t-butyl-1-cyclopentadienyl)titanium dichloride
dimethylsilanediylbis(2-propyl-4-trimethylsilyl-1-cyclopentadienyl)titanium dichloride
dimethylsilanediylbis(2-propyl-4-phenyl-1-cyclopentadienyl)titanium dichloride
dimethylsilanediylbis(2-butyl-4-methyl-1-cyclopentadienyl)titanium dichloride
dimethylsilanediylbis(2-butyl-4-ethyl-1-cyclopentadienyl)titanium dichloride
dimethylsilanediylbis(2-butyl-4-propyl-1-cyclopentadienyl)titanium dichloride
dimethylsilanediylbis(2-butyl-4-butyl-1-cyclopentadienyl)titanium dichloride
dimethylsilanediylbis(2-butyl-4-i-propyl-1-cyclopentadienyl)titanium dichloride
dimethylsilanediylbis(2-butyl-4-i-butyl-1-cyclopentadienyl)titanium dichloride
dimethylsilanediylbis(2-butyl-4-t-butyl-1-cyclopentadienyl)titanium dichloride
dimethylsilanediylbis(2-butyl-4-trimethylsilyl-1-cyclopentadienyl)titanium dichloride
dimethylsilanediylbis(2-butyl-4-phenyl-1-cyclopentadienyl)titanium dichloride
dimethylsilanediylbis(2-i-propyl-4-methyl-1-cyclopentadienyl)titanium dichloride
dimethylsilanediylbis(2-i-propyl-4-ethyl-1-cyclopentadienyl)titanium dichloride
dimethylsilanediylbis(2-i-propyl-4-propyl-1-cyclopentadienyl)titanium dichloride
dimethylsilanediylbis(2-i-propyl-4-butyl-1-cyclopentadienyl)titanium dichloride
dimethylsilanediylbis(2-i-propyl-4-i-propyl-1-cyclopentadienyl)titanium dichloride
dimethylsilanediylbis(2-i-propyl-4-i-butyl-1-cyclopentadienyl)titanium dichloride
dimethylsilanediylbis(2-i-propyl-4-t-butyl-1-cyclopentadienyl)titanium dichloride
dimethylsilanediylbis(2-i-propyl-4-trimethylsilyl-1-cyclopentadienyl)titanium dichloride
dimethylsilanediylbis(2-i-propyl-4-phenyl-1-cyclopentadienyl)titanium dichloride
dimethylsilanediylbis(2-t-butyl-4-methyl-1-cyclopentadienyl)titanium dichloride
dimethylsilanediylbis(2-t-butyl-4-ethyl-1-cyclopentadienyl)titanium dichloride
dimethylsilanediylbis(2-t-butyl-4-propyl-1-cyclopentadienyl)titanium dichloride
dimethylsilanediylbis(2-t-butyl-4-butyl-1-cyclopentadienyl)titanium dichloride
dimethylsilanediylbis(2-t-butyl-4-i-propyl-1-cyclopentadienyl)titanium dichloride
dimethylsilanediylbis(2-t-butyl-4-i-butyl-1-cyclopentadienyl)titanium dichloride
dimethylsilanediylbis(2-t-butyl-4-t-butyl-1-cyclopentadienyl)titanium dichloride
dimethylsilanediylbis(2-t-butyl-4-trimethylsilyl-1-cyclopentadienyl)titanium dichloride
dimethylsilanediylbis(2-t-butyl-4-phenyl-1-cyclopentadienyl)titanium dichloride
dimethylsilanediylbis(2-trimethylsilyl-4-methyl-1-cyclopentadienyl)titanium dichloride
dimethylsilanediylbis(2-trimethylsilyl-4-ethyl-1-cyclopentadienyl)titanium dichloride
dimethylsilanediylbis(2-trimethylsilyl-4-propyl-1-cyclopentadienyl)titanium dichloride
dimethylsilanediylbis(2-trimethylsilyl-4-butyl-1-cyclopentadienyl)titanium dichloride
dimethylsilanediylbis(2-trimethylsilyl-4-i-propyl-1-cyclopentadienyl)titanium dichloride
dimethylsilanediylbis(2-trimethylsilyl-4-i-butyl-1-cyclopentadienyl)titanium dichloride
dimethylsilanediylbis(2-trimethylsilyl-4-t-butyl-1-cyclopentadienyl)titanium dichloride
dimethylsilanediylbis(2-trimethylsilyl-4-trimethylsilyl-1-cyclopentadienyl)titanium dichloride
dimethylsilanediylbis(2-trimethylsilyl-4-phenyl-1-cyclopentadienyl)titanium dichloride
dimethylsilanediylbis(2-phenyl-4-methyl-1-cyclopentadienyl)titanium dichloride
dimethylsilanediylbis(2-phenyl-4-ethyl-1-cyclopentadienyl)titanium dichloride
dimethylsilanediylbis(2-phenyl-4-propyl-1-cyclopentadienyl)titanium dichloride
dimethylsilanediylbis(2-phenyl-4-butyl-1-cyclopentadienyl)titanium dichloride
dimethylsilanediylbis(2-phenyl-4-i-propyl-1-cyclopentadienyl)titanium dichloride
dimethylsilanediylbis(2-phenyl-4-i-butyl-1-cyclopentadienyl)titanium dichloride dimethylsilanediylbis(2-phenyl-4-t-butyl-1-cyclopentadienyl)titanium dichloride
dimethylsilanediylbis(2-phenyl-4-trimethylsilyl-1-cyclopentadienyl)titanium dichloride
dimethylsilanediylbis(2-phenyl-4-phenyl-1-cyclopentadienyl)titanium dichloride
dimethylsilanediylbis(2-methyl-1-indenyl)titanium dichloride
dimethylsilanediylbis(2-ethyl-1-indenyl)titanium dichloride
dimethylsilanediylbis(2-propyl-1-indenyl)titanium dichloride
dimethylsilanediylbis(2-butyl-1-indenyl)titanium dichloride
dimethylsilanediylbis(2-i-propyl-1-indenyl)titanium dichloride
dimethylsilanediylbis(2-t-butyl-1-indenyl)titanium dichloride
dimethylsilanediylbis(2-trimethylsilyl-1-indenyl)titanium dichloride
dimethylsilanediylbis(2-phenyl-1-indenyl)titanium dichloride
dimethylsilanediylbis(2-methyl-4,5,6,7-tetrahydro-1-indenyl)titanium dichloride
dimethylsilanediylbis(2-ethyl-4,5,6,7-tetrahydro-1-indenyl)titanium dichloride
dimethylsilanediylbis(2-propyl-4,5,6,7-tetrahydro-1-indenyl)titanium dichloride
dimethylsilanediylbis(2-butyl-4,5,6,7-tetrahydro-1-indenyl)titanium dichloride
dimethylsilanediylbis(2-i-propyl-4,5,6,7-tetrahydro-1-indenyl)titanium dichloride
dimethylsilanediylbis(2-t-butyl-4,5,6,7-tetrahydro-1-indenyl)titanium dichloride
dimethylsilanediylbis(2-trimethylsilyl-4,5,6,7-tetrahydro-1-indenyl)titanium dichloride
dimethylsilanediylbis(2-phenyl-4,5,6,7-tetrahydro-1-indenyl)titanium dichloride
dimethylsilanediylbis(2-methyl-4,7-dimethyl-1-indenyl)titanium dichloride
dimethylsilanediylbis(2-ethyl-4,7-dimethyl-1-indenyl)titanium dichloride
dimethylsilanediylbis(2-propyl-4,7-dimethyl-1-indenyl)titanium dichloride
dimethylsilanediylbis(2-butyl-4,7-dimethyl-1-indenyl)titanium dichloride
dimethylsilanediylbis(2-i-propyl-4,7-dimethyl-1-indenyl)titanium dichloride
dimethylsilanediylbis(2-t-butyl-4,7-dimethyl-1-indenyl)titanium dichloride
dimethylsilanediylbis(2-trimethylsilyl-4,7-dimethyl-1-indenyl)titanium dichloride
dimethylsilanediylbis(2-phenyl-4,7-dimethyl-1-indenyl)titanium dichloride
dimethylsilanediylbis(2-methyl-4,6-di-i-propyl-1-indenyl)titanium dichloride
dimethylsilanediylbis(2-ethyl-4,6-di-i-propyl-1-indenyl)titanium dichloride
dimethylsilanediylbis(2-propyl-4,6-di-i-propyl-1-indenyl)titanium dichloride
dimethylsilanediylbis(2-butyl-4,6-di-i-propyl-1-indenyl)titanium dichloride
dimethylsilanediylbis(2-i-propyl-4,6-di-i-propyl-1-indenyl)titanium dichloride
dimethylsilanediylbis(2-t-butyl-4,6-di-i-propyl-1-indenyl)titanium dichloride
dimethylsilanediylbis(2-trimethylsilyl-4,6-di-i-propyl-1-indenyl)titanium dichloride
dimethylsilanediylbis(2-phenyl-4,6-di-i-propyl-1-indenyl)titanium dichloride
dimethylsilanediylbis(2-methyl-1-benzindenyl)titanium dichloride
dimethylsilanediylbis(2-ethyl-1-benzindenyl)titanium dichloride
dimethylsilanediylbis(2-propyl-1-benzindenyl)titanium dichloride
dimethylsilanediylbis(2-butyl-1-benzindenyl)titanium dichioride
dimethylsilanediylbis(2-i-propyl-1-benzindenyl)titanium dichloride
dimethylsilanediylbis(2-t-butyl-1-benzindenyl)titanium dichloride
dimethylsilanediylbis(2-trimethylsilyl-1-benzindenyl)titanium dichloride
dimethylsilanediylbis(2-phenyl-1-benzindenyl)titanium dichloride
dimethylsilanediylbis(2-methyl-4-phenyl-1-indenyl)titanium dichloride
dimethylsilanediylbis(2-ethyl-4-phenyl-1-indenyl)titanium dichloride
dimethylsilanediylbis(2-propyl-4-phenyl-1-indenyl)titanium dichloride
dimethylsilanediylbis(2-butyl-4-phenyl-1-indenyl)titanium dichloride
dimethylsilanediylbis(2-i-propyl-4-phenyl-1-indenyl)titanium dichloride
dimethylsilanediylbis(2-t-butyl-4-phenyl-1-indenyl)titanium dichloride
dimethylsilanediylbis(2-trimethylsilyl-4-phenyl-1-indenyl)titanium dichloride
dimethylsilanediylbis(2-phenyl-4-phenyl-1-indenyl)titanium dichloride
dimethylsilanediylbis(2-methyl-4-naphthyl-1-indenyl)titanium dichloride
dimethylsilanediylbis(2-ethyl-4-naphthyl-1-indenyl)titanium dichloride
dimethylsilanediylbis(2-propyl-4-naphthyl-1-indenyl)titanium dichloride
dimethylsilanediylbis(2-butyl-4-naphthyl-1-indenyl)titanium dichloride
dimethylsilanediylbis(2-i-propyl-4-naphthyl-1-indenyl)titanium dichloride
dimethylsilanediylbis(2-t-butyl-4-naphthyl-1-indenyl)titanium dichloride
dimethylsilanediylbis(2-trimethylsilyl-4-naphthyl-1-indenyl)titanium dichloride
dimethylsilanediylbis(2-phenyl-4-naphthyl-1-indenyl)titanium dichloride
dimethylsilanediylbis(2-methyl-4-methyl-1-cyclopentadienyl)hafnium dichloride
dimethylsilanediylbis(2-methyl-4-ethyl-1-cyclopentadienyl)hafnium dichloride
dimethylsilanediylbis(2-methyl-4-propyl-1-cyclopentadienyl)hafnium dichloride
dimethylsilanediylbis(2-methyl-4-butyl-1-cyclopentadienyl)hafnium dichloride
dimethylsilanediylbis(2-methyl-4-i-propyl-1-cyclopentadienyl)hafnium dichloride
dimethylsilanediylbis(2-methyl-4-i-butyl-1-cyclopentadienyl)hafnium dichloride
dimethylsilanediylbis(2-methyl-4-t-butyl-1-cyclopentadienyl)hafnium dichloride
dimethylsilanediylbis(2-methyl-4-trimethylsilyl-1-cyclopentadienyl)hafnium dichloride
dimethylsilanediylbis(2-methyl-4-phenyl-1-cyclopentadienyl)hafnium dichloride
dimethylsilanediylbis(2-ethyl-4-methyl-1-cyclopentadienyl)hafnium dichloride dimethylsilanediylbis(2-ethyl-4-ethyl-1-cyclopentadienyl)hafnium dichloride
dimethylsilanediylbis(2-ethyl-4-propyl-1-cyclopentadienyl)hafnium dichloride
dimethylsilanediylbis(2-ethyl-4-butyl-1-cyclopentadienyl)hafnium dichloride
dimethylsilanediylbis(2-ethyl-4-i-propyl-1-cyclopentadienyl)hafnium dichloride
dimethylsilanediylbis(2-ethyl-4-i-butyl-1-cyclopentadienyl)hafnium dichloride
dimethylsilanediylbis(2-ethyl-4-t-butyl-1-cyclopentadienyl)hafnium dichloride
dimethylsilanediylbis(2-ethyl-4-trimethylsilyl-1-cyclopentadienyl)hafnium dichloride
dimethylsilanediylbis(2-ethyl-4-phenyl-1-cyclopentadienyl)hafnium dichloride
dimethylsilanediylbis(2-propyl-4-methyl-1-cyclopentadienyl)hafnium dichloride
dimethylsilanediylbis(2-propyl-4-ethyl-1-cyclopentadienyl)hafnium dichloride
dimethylsilanediylbis(2-propyl-4-propyl-1-cyclopentadienyl)hafnium dichloride
dimethylsilanediylbis(2-propyl-4-butyl-1-cyclopentadienyl)hafnium dichloride
dimethylsilanediylbis(2-propyl-4-i-propyl-1-cyclopentadienyl)hafnium dichloride
dimethylsilanediylbis(2-propyl-4-i-butyl-1-cyclopentadienyl)hafnium dichloride
dimethylsilanediylbis(2-propyl-4-t-butyl-1-cyclopentadienyl)hafnium dichloride
dimethylsilanediylbis(2-propyl-4-trimethylsilyl-1-cyclopentadienyl)hafnium dichloride
dimethylsilanediylbis(2-propyl-4-phenyl-1-cyclopentadienyl)hafnium dichloride
dimethylsilanediylbis(2-butyl-4-methyl-1-cyclopentadienyl)hafnium dichloride
dimethylsilanediylbis(2-butyl-4-ethyl-1-cyclopentadienyl)hafnium dichloride
dimethylsilanediylbis(2-butyl-4-propyl-1-cyclopentadienyl)hafnium dichloride
dimethylsilanediylbis(2-butyl-4-butyl-1-cyclopentadienyl)hafnium dichloride
dimethylsilanediylbis(2-butyl-4-i-propyl-1-cyclopentadienyl)hafnium dichloride
dimethylsilanediylbis(2-butyl-4-i-butyl-1-cyclopentadienyl)hafnium dichloride
dimethylsilanediylbis(2-butyl-4-t-butyl-1-cyclopentadienyl)hafnium dichloride
dimethylsilanediylbis(2-butyl-4-trimethylsilyl-1-cyclopentadienyl)hafnium dichloride
dimethylsilanediylbis(2-butyl-4-phenyl-1-cyclopentadienyl)hafnium dichloride
dimethylsilanediylbis(2-i-propyl-4-methyl-1-cyclopentadienyl)hafnium dichloride
dimethylsilanediylbis(2-i-propyl-4-ethyl-1-cyclopentadienyl)hafnium dichloride
dimethylsilanediylbis(2-i-propyl-4-propyl-1-cyclopentadienyl)hafnium dichloride
dimethylsilanediylbis(2-i-propyl-4-butyl-1-cyclopentadienyl)hafnium dichloride
dimethylsilanediylbis(2-i-propyl-4-i-propyl-1-cyclopentadienyl)hafnium dichloride
dimethylsilanediylbis(2-i-propyl-4-i-butyl-1-cyclopentadienyl)hafnium dichloride
dimethylsilanediylbis(2-i-propyl-4-t-butyl-1-cyclopentadienyl)hafnium dichloride
dimethylsilanediylbis(2-i-propyl-4-trimethylsilyl-1-cyclopentadienyl)hafnium dichloride
dimethylsilanediylbis(2-i-propyl-4-phenyl-1-cyclopentadienyl)hafnium dichloride
dimethylsilanediylbis(2-t-butyl-4-methyl-1-cyclopentadienyl)hafnium dichloride
dimethylsilanediylbis(2-t-butyl-4-ethyl-1-cyclopentadienyl)hafnium dichloride
dimethylsilanediylbis(2-t-butyl-4-propyl-1-cyclopentadienyl)hafnium dichloride
dimethylsilanediylbis(2-t-butyl-4-butyl-1-cyclopentadienyl)hafnium dichloride
dimethylsilanediylbis(2-t-butyl-4-i-propyl-1-cyclopentadienyl)hafnium dichloride
dimethylsilanediylbis(2-t-butyl-4-i-butyl-1-cyclopentadienyl)hafnium dichloride
dimethylsilanediylbis(2-t-butyl-4-t-butyl-1-cyclopentadienyl)hafnium dichloride
dimethylsilanediylbis(2-t-butyl-4-trimethylsilyl-1-cyclopentadienyl)hafnium dichloride
dimethylsilanediylbis(2-t-butyl-4-phenyl-1-cyclopentadienyl)hafnium dichloride
dimethylsilanediylbis(2-trimethylsilyl-4-methyl-1-cyclopentadienyl)hafnium dichloride
dimethylsilanediylbis(2-trimethylsilyl-4-ethyl-1-cyclopentadienyl)hafnium dichloride
dimethylsilanediylbis(2-trimethylsilyl-4-propyl-1-cyclopentadienyl)hafnium dichloride
dimethylsilanediylbis(2-trimethylsilyl-4-butyl-1-cyclopentadienyl)hafnium dichloride
dimethylsilanediylbis(2-trimethylsilyl-4-i-propyl-1-cyclopentadienyl)hafnium dichloride
dimethylsilanediylbis(2-trimethylsilyl-4-i-butyl-1-cyclopentadienyl)hafnium dichloride
dimethylsilanediylbis(2-trimethylsilyl-4-t-butyl-1-cyclopentadienyl)hafnium dichloride
dimethylsilanediylbis(2-trimethylsilyl-4-trimethylsilyl-1-cyclopentadienyl)hafnium dichloride
dimethylsilanediylbis(2-trimethylsilyl-4-phenyl-1-cyclopentadienyl)hafnium dichloride
dimethylsilanediylbis(2-phenyl-4-methyl-1-cyclopentadienyl)hafnium dichloride
dimethylsilanediylbis(2-phenyl-4-ethyl-1-cyclopentadienyl)hafnium dichloride
dimethylsilanediylbis(2-phenyl-4-propyl-1-cyclopentadienyl)hafnium dichloride
dimethylsilanediylbis(2-phenyl-4-butyl-1-cyclopentadienyl)hafnium dichloride
dimethylsilanediylbis(2-phenyl-4-i-propyl-1-cyclopentadienyl)hafnium dichloride
dimethylsilanediylbis(2-phenyl-4-i-butyl-1-cyclopentadienyl)hafnium dichloride
dimethylsilanediylbis(2-phenyl-4-t-butyl-1-cyclopentadienyl)hafnium dichloride
dimethylsilanediylbis(2-phenyl-4-trimethylsilyl-1-cyclopentadienyl)hafnium dichloride
dimethylsilanediylbis(2-phenyl-4-phenyl-1-cyclopentadienyl)hafnium dichloride
dimethylsilanediylbis(2-methyl-1-indenyl)hafnium dichloride
dimethylsilanediylbis(2-ethyl-1-indenyl)hafnium dichloride
dimethylsilanediylbis(2-propyl-1-indenyl)hafnium dichloride
dimethylsilanediylbis(2-butyl-1-indenyl)hafnium dichloride
dimethylsilanediylbis(2-i-propyl-1-indenyl)hafnium dichloride
dimethylsilanediylbis(2-t-butyl-1-indenyl)hafnium dichloride
dimethylsilanediylbis(2-trimethylsilyl-1-indenyl)hafnium dichloride dimethylsilanediylbis(2-phenyl-1-indenyl)hafnium dichloride
dimethylsilanediylbis(2-methyl-4,5,6,7-tetrahydro-1-indenyl)hafnium dichloride
dimethylsilanediylbis(2-ethyl-4,5,6,7-tetrahydro-1-indenyl)hafnium dichloride
dimethylsilanediylbis(2-propyl-4,5,6,7-tetrahydro-1-indenyl)hafnium dichloride
dimethylsilanediylbis(2-butyl-4,5,6,7-tetrahydro-1-indenyl)hafnium dichloride
dimethylsilanediylbis(2-i-propyl-4,5,6,7-tetrahydro-1-indenyl hafnium dichloride
dimethylsilanediylbis(2-t-butyl-4,5,6,7-tetrahydro-1-indenyl)hafnium dichloride
dimethylsilanediylbis(2-trimethylsilyl-4,5,6,7-tetrahydro-1-indenyl)hafnium dichloride
dimethylsilanediylbis(2-phenyl-4,5,6,7-tetrahydro-1-indenyl)hafnium dichloride
dimethylsilanediylbis(2-methyl-4,7-dimethyl-1-indenyl)hafnium dichloride
dimethylsilanediylbis(2-ethyl-4,7-dimethyl-1-indenyl)hafnium dichloride
dimethylsilanediylbis(2-propyl-4,7-dimethyl-1-indenyl)hafnium dichloride
dimethylsilanediylbis(2-butyl-4,7-dimethyl-1-indenyl)hafnium dichloride
dimethylsilanediylbis(2-i-propyl-4,7-dimethyl-1-indenyl)hafnium dichloride
dimethylsilanediylbis(2-t-butyl-4,7-dimethyl-1-indenyl)hafnium dichloride
dimethylsilanediylbis(2-trimethylsilyl-4,7-dimethyl-1-indenyl)hafnium dichloride
dimethylsilanediylbis(2-phenyl-4,7-dimethyl-1-indenyl)hafnium dichloride
dimethylsilanediylbis(2-methyl-4,6-di-i-propyl-1-indenyl)hafnium dichloride
dimethylsilanediylbis(2-ethyl-4,6-di-i-propyl-1-indenyl)hafnium dichloride
dimethylsilanediylbis(2-propyl-4,6-di-i-propyl-1-indenyl)hafnium dichloride
dimethylsilanediylbis(2-butyl-4,6-di-i-propyl-1-indenyl)hafnium dichloride
dimethylsilanediylbis(2-i-propyl-4,6-di-i-propyl-1-indenyl)hafnium dichloride
dimethylsilanediylbis(2-t-butyl-4,6-di-i-propyl-1-indenyl)hafnium dichloride
dimethylsilanediylbis(2-trimethylsilyl-4,6-di-i-propyl-1-indenyl)hafnium dichloride
dimethylsilanediylbis(2-phenyl-4,6-di-i-propyl-1-indenyl)hafnium dichloride
dimethylsilanediylbis(2-methyl-1-benzindenyl)hafnium dichloride
dimethylsilanediylbis(2-ethyl-1-benzindenyl)hafnium dichloride
dimethylsilanediylbis(2-propyl-1-benzindenyl)hafnium dichloride
dimethylsilanediylbis(2-butyl-1-benzindenyl)hafnium dichloride
dimethylsilanediylbis(2-i-propyl-1-benzindenyl)hafnium dichloride
dimethylsilanediylbis(2-t-butyl-1-benzindenyl)hafnium dichloride
dimethylsilanediylbis(2-trimethylsilyl-1-benzindenyl)hafnium dichloride
dimethylsilanediylbis(2-phenyl-1-benzindenyl)hafnium dichloride
dimethylsilanediylbis(2-methyl-4-phenyl-1-indenyl)hafnium dichloride
dimethylsilanediylbis(2-ethyl-4-phenyl-1-indenyl)hafnium dichloride
dimethylsilanediylbis(2-propyl-4-phenyl-1-indenyl)hafnium dichloride
dimethylsilanediylbis(2-butyl-4-phenyl-1-indenyl)hafnium dichloride
dimethylsilanediylbis(2-i-propyl-4-phenyl-1-indenyl)hafnium dichloride
dimethylsilanediylbis(2-t-butyl-4-phenyl-1-indenyl)hafnium dichloride
dimethylsilanediylbis(2-trimethylsilyl-4-phenyl-1-indenyl)hafnium dichloride
dimethylsilanediylbis(2-phenyl-4-phenyl-1-indenyl)hafnium dichloride
dimethylsilanediylbis(2-methyl-4-naphthyl-1-indenyl)hafnium dichloride
dimethylsilanediylbis(2-ethyl-4-naphthyl-1-indenyl)hafnium dichloride
dimethylsilanediylbis(2-propyl-4-naphthyl-1-indenyl)hafnium dichloride
dimethylsilanediylbis(2-butyl-4-naphthyl-1-indenyl)hafnium dichloride
dimethylsilanediylbis(2-i-propyl-4-naphthyl-1-indenyl)hafnium dichloride
dimethylsilanediylbis(2-t-butyl-4-naphthyl-1-indenyl)hafnium dichloride
dimethylsilanediylbis(2-trimethylsilyl-4-naphthyl-1-indenyl)hafnium dichloride
dimethylsilanediylbis(2-phenyl-4-naphthyl-1-indenyl)hafnium dichloride
and also the analogous diphenylsilylene-bridged complexes.

Such complexes can be synthesized by methods known per se, with preference being given to reacting the appropriately substituted cyclic hydrocarbon anions with halides of titanium, zirconium, hafnium, vanadium, niobium or tantalum. Examples of appropriate preparative methods are described, inter alia, in Brintzinger et al., Journal of Organometallic Chemistry, 369 (1989), pp. 359–370.

The ansa-metallocene complexes prepared by these customary methods are usually obtained in an rac:meso ratio of about 1:1.

In the photochemical conversion process of the present invention, the mixture of rac and meso forms can be irradiated electromagnetically with a wavelength of less than 1000 nm, preferably from 50 to 500 nm, for example using a UV lamp. It has been found to be useful to carry out the radiation at from −80 to +100° C. for from 0.01 to 72 hours.

According to the invention, the photochemical conversion is carried out in the presence of a chiral auxiliary reagent. Chiral auxiliary reagents which are particularly useful are those which are bifunctional, in particular dialkoxides.

Particularly useful dialkoxides are those derived from dialcohols of the formula II

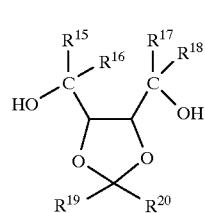

II where the substituents have the following meanings:
$R^{15}$ to $R^{18}$ are hydrogen, $C_1$–$C_{10}$-alkyl or $C_6$–$C_{15}$-aryl,
$R^{19}$ and $R^{20}$ are hydrogen, $C_1$–$C_{10}$-alkyl, $C_3$–$C_{10}$-cycloalkyl or $C_6$–$C_{15}$-aryl, or $R^{19}$ and $R^{20}$ together form a $C_3$–$C_{10}$-cycloalkyl ring, or from

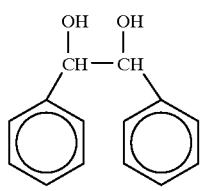

or from

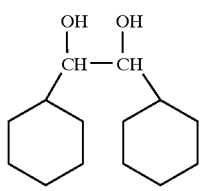

or, particularly preferably, from binaphthols, in particular from 1,1'-bi-2-naphthol

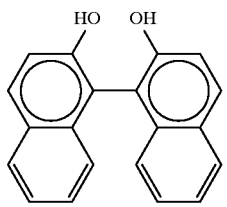

The chiral dialcohols are known per se and are commercially available. The dialkoxide is then prepared from these dialcohols by simple reaction with a suitable base such as n-butyllithium and is then used as chiral auxiliary reagent. Of course, other chiral compounds such as dimercaptans or diamines are also suitable as chiral auxiliary reagents. These compounds and methods of preparing them are likewise known per se.

Mixtures of various chiral auxiliary reagents can likewise be used.

The molar ratio of chiral auxiliary reagent to the ansa-metallocene complex is preferably from 0.1:1 to 10:1, in particular from 0.5:1 to 1.5:1.

It has been found to be particularly useful to carry out the conversion in the presence of a solvent. Preference is given to using organic solvents such as tetrahydrofuran, $CH_2Cl_2$, $CHCl_3$ and, in particular, aromatic hydrocarbons such as benzene, deuterated benzene and toluene. It is also possible to use solvent mixtures.

The following method has been found to be particularly useful: a mixture of rac and meso forms of an ansa-metallocene complex or only the meso form of an ansa-metallocene complex, the chiral auxiliary reagent and the solvent are placed in the irradiation vessel of a UV irradiation apparatus, preferably under an inert gas atmosphere. During irradiation, the chiral auxiliary reagent reacts exclusively with the rac form of the ansa-metallocene complex to form a photo-inactive product while the meso form isomerizes to the rac form. The photoinactive product can then be converted into the rac-dichloride of the ansa-metallocene complex by methods known per se, as described in Brintzinger et al., Journal of Organometallic Chemistry, 232 (1982), pp. 233–247, by reaction with, for example, methyllithium and subsequent cleavage with gaseous HCl.

Alternatively, the alkoxide can also, as described in JP-A 05287017, be alkylated by reaction with a metal alkyl and activated in situ with a cation former to give the polymerization-active metallocenium cation. In the preferred use of ansa-metallocene complexes as catalysts for preparing polyolefins, the photo-inactive product (eg. Metallocene binaphthoxide) can also be reacted directly with customary cocatalysts such as aluminoxanes for use as active catalyst components, as described in Waymouth et al., J. Am. Chem. Soc., 112 (1990), pp. 4911–4914.

The process of the present invention gives a quantitative conversion of the achiral meso form of an ansa-metallocene complex into the chiral rac form and is both simple to carry out and inexpensive. The chiral rac form of an ansa-metallocene complex is used, first and foremost as catalyst for the stereospecific polymerization of olefins.

EXAMPLES

The photochemical conversion was carried out by irradiation with a Phillips HPK 125W mercury vapor lamp.

Example 1

Preparation of rac-dimethylsilanediylbis(2-methyl-4-tert-butyl-1-cyclopentadienyl)zirconium 1,1'-bi-2-naphthoxide by conversion of an rac/meso mixture 24 mg (0.05 mmol) of an rac/meso mixture (molar ratio 1:1) of dimethylsilanediylbis(2-methyl-4-tert-butyl-1-cyclopentadienyl)zirconium dichloride, 21 mg (0,07 mmol) of dilithium 1,1'-bi-2-naphthoxide and 0.4 ml of $C_6D_6$ were placed in an NMR tube, frozen and the tube was flame-sealed under a high vacuum. The tube was subsequently fixed to the Hg vapor lamp and irradiated at 40° C. for 24 hours. The quantitative conversion of rac-dimethylsilanediylbis(2-methyl-4-tert-butyl-1-cyclopentadienyl)zirconium 1,1'-bi-2-naphthoxide was able to be confirmed by NMR-spectroscopy.

$^1$H-NMR, signal positions relative to TMS (tetramethylsilane) in $C_6D_6$:

0.58 ppm (s, 6H); 0.76 ppm (s, 18H); 2.11 ppm (s, 2H); 5.59 ppm (d, 2H); 5.96 ppm (d, 2H); 6.8–7.3 and 7.7–7.82 ppm (d, 12H).

Example 2

Preparation of rac-dimethylsilanediylbis(2-methyl-4-phenyl-1-cyclopentadienyl)zirconium 1,1'-bi-2-naphthoxide by conversion of the meso form 528 mg (1 mmol) of meso-dimethylsilanediylbis(2-methyl-4-phenyl-1-cyclopentadienyl)zirconium dichloride and 328 mg (1.2 mmol)of dilithium 1,1'-bi-2-naphthoxide were placed in an irradiation vessel of the Hg-vapor lamp and suspended in 50 ml of absolute toluene. The suspension was mixed by passing a gentle stream of argon through it and was irradiated for 5 hours at 30° C. This gave a pure yellow solution in which LiCl formed was suspended. The LiCl was removed by filtration (under protective gas) through kieselguhr and the solvent was taken off from the filtrate. Washing with pentane and drying under reduced pressure left 690 mg of rac-dimethylsilanediylbis(2-methyl-4-phenyl-1-cyclopentadienyl)zirconium 1,1'-bi-2-naphthoxide [yield: 93%; $^1$H-NMR [$C_6D_6$]: 0.66 ppm (s, 6H), 2,07 ppm (s, 6H), 5.92/5.93 ppm (d, 2H), 6.22/6.23 ppm (d, 2H), 6.45–7.8 ppm (m, 22H)].

Comparative Example VI

Reaction of rac/meso-dimethylsilanediylbis(2-methyl-4-phenyl-1-cyclopentadienyl)zirconium dichloride with dilithium 1,1'-bi-2-naphthoxide without irradiation.

26 mg (0.05 mmol) of dimethylsilanediylbis(2-methyl-4-phenyl-1-cyclopentadienyl)zirconium dichloride (rac/meso molar ratio=1:1)) and 21 mg (0.07 mmol) of dilithium 1,1'-bi-2-naphthoxide were weighed into an NMR-tube and dissolved in 0.4 ml of $C_6D_6$. After the solution had been frozen, the tube was flame-sealed under a high vacuum and shaken well after thawing.

A reaction of the rac diastereomer with the binaphthoxide could be followed by NMR spectroscopy and was complete after 6 hours: $^1$H-NMR [$C_6D_6$]: 0.66 ppm (s, 6H), 2.07 ppm (s, 6H), 5.92/5.93 ppm (d, 2H), 6.22/6.23 ppm (d, 2H), 6.45–7.8 ppm (m, 22H). In contrast, the signals of the meso diastereomer were unchanged.

We claim:

1. A process for converting the achiral meso form of an ansa-metallocene complex into the chiral rac form, wherein the conversion is carried out photochemically in the presence of a chiral auxiliary reagent.

2. The process of claim 1, wherein the conversion is carried out in the presence of an organic solvent.

3. The process of claim 1, wherein the photochemical conversion is carried out using electromagnetic radiation having a wavelength of less than 1000 nm.

4. The process of claim 1, wherein the chiral auxiliary reagent is bifunctional.

5. The process of claim 1, wherein the chiral auxiliary reagent used is a dialkoxide.

6. The process of claim 1, wherein the chiral auxiliary reagent used is the racemate of a binaphthoxide.

7. The process of claim 1, wherein the ansa-metallocene complex used has the formula I

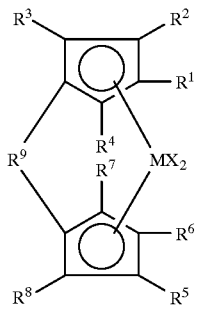

I where the substituents and indices have the following meanings:

M is titanium, zirconium, hafnium, vanadium, niobium or tantalum,

X is fluorine, chlorine, bromine, iodine, hydrogen, $C_1$–$C_{10}$-alkyl, $C_6$–$C_{15}$-aryl or —$OR^{10}$, where $R^{10}$ is $C_1$–$C_{10}$-alkyl, $C_6$–$C_{15}$-aryl, alkylaryl, arylalkyl, fluoroalkyl or fluoroaryl having 1 to 10 carbon atoms in the alkyl radical and from 6 to 20 carbon atoms in the aryl radical, $R^1$ to $R^8$ are hydrogen, $C_1$–$C_{10}$-alkyl, 5- to 7-membered cycloalkyl which may in turn bear a $C_1$–$C_{10}$-alkyl group as substituent, $C_6$–$C_{15}$-aryl or arylalkyl, where two adjacent radicals may together form a cyclic group having from 4 to 15 carbon atoms, or $Si(R^{11})_3$ where $R^{11}$ is $C_1$–$C_{10}$-alkyl, $C_6$–$C_{15}$-aryl or $C_3$–$C_{10}$-cycloalkyl, $R^9$ is

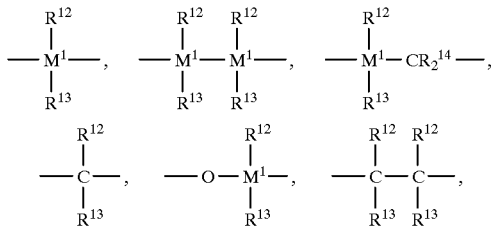

=$BR^{12}$, =$AlR^{12}$, —Ge—, —Sn—, —O—, —S—, =SO, =$SO_2$, =$NR^{12}$, =CO, =$PR^{12}$ or =$P(O)R^{12}$, where $R^{12}$, $R^{13}$ and $R^{14}$ are identical or different and are hydrogen, halogen, $C_1$–$C_{10}$-alkyl, $C_1$–$C_{10}$-fluoroalkyl, $C_6$–$C_{10}$-fluoroaryl, $C_6$–$C_{10}$-aryl, $C_1$–$C_{10}$-alkoxy, $C_2$–$C_{10}$-alkenyl, $C_7$–$C_{40}$-arylalkyl, $C_8$–$C_{40}$-arylalkenyl or $C_7$–$C_{40}$-alkylaryl, or $R^{12}$ and $R^{13}$ or $R^{12}$ and $R^{14}$ in each case together with the atoms connecting them form a ring, and $M^1$ is silicon, germanium or tin.

8. The process of claim 1, wherein the ansa-metallocene complex is substituted in the 2 position of the cyclopentadienyl rings.

9. The process of claim 1, wherein the ansa-metallocene complex used is a silyl-bridged complex.

* * * * *